US010370665B2

(12) United States Patent
Miller et al.

(10) Patent No.: US 10,370,665 B2
(45) Date of Patent: Aug. 6, 2019

(54) COMPOSITIONS AND METHODS FOR TREATING CANCER, INHIBITING CELL PROLIFERATION, AND INDUCING CELL DEATH

(71) Applicant: UNIVERSITY OF LOUISVILLE RESEARCH FOUNDATION, INC., Louisville, KY (US)

(72) Inventors: Donald M. Miller, Louisville, KY (US); Shelia D. Thomas, Louisville, KY (US); Alexandra Sokolova, Louisville, KY (US); Francine Rezzoug, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 0 days.

(21) Appl. No.: 15/122,663

(22) PCT Filed: Mar. 4, 2015

(86) PCT No.: PCT/US2015/018776
§ 371 (c)(1),
(2) Date: Aug. 31, 2016

(87) PCT Pub. No.: WO2015/134634
PCT Pub. Date: Sep. 11, 2015

(65) Prior Publication Data
US 2017/0067057 A1   Mar. 9, 2017

Related U.S. Application Data

(60) Provisional application No. 61/947,752, filed on Mar. 4, 2014.

(51) Int. Cl.
A61K 48/00 (2006.01)
C07H 21/02 (2006.01)
C07H 21/04 (2006.01)
C12N 15/113 (2010.01)
A61K 31/7088 (2006.01)
A61K 45/06 (2006.01)

(52) U.S. Cl.
CPC ...... *C12N 15/1137* (2013.01); *A61K 31/7088* (2013.01); *A61K 45/06* (2013.01); *C12N 2310/13* (2013.01); *C12N 2310/151* (2013.01); *C12N 2310/18* (2013.01); *C12N 2320/31* (2013.01)

(58) Field of Classification Search
CPC . C12N 15/111; C12N 15/113; C12N 2310/11; A61K 31/713
See application file for complete search history.

(56) References Cited

U.S. PATENT DOCUMENTS 4,675,187 A    6/1987  Konishi et al.
2011/0213019 A1  9/2011  Miller et al.

FOREIGN PATENT DOCUMENTS

| JP | 201460992 A | 4/2014 |
| WO | 2003087317 A2 | 10/2003 |
| WO | 2007128968 A1 | 11/2007 |
| WO | 2013122178 A1 | 8/2013 |

OTHER PUBLICATIONS

Elbashir et al. (The EMBO Journal, vol. 20, No. 23, pp. 6877-6888, 2001).*
Alan K. Todd et al, "Highly prevalent putative quadruplex sequence motifs in human DNA," Nucleic Acids Research, vol. 33, No. 9, pp. 2901-2907. 2005.
Ambrus et al., "Solution Structure of the Biologically Relevant G-Quadruplex Element in the Human Cmyc Promoter. Implications for G-Quadruplex Stabilization" Biochemistry (2005) vol. 44, pp. 2048-2058 (doi: 10.1021/bi048242p).
Dailey et al., "Resolution and Characterization of the Structural Polymorphism of a Single Quadruplex-Forming Sequence" Nucleic Acids Research (2010) vol. 38, pp. 4877-4888 (doi: 10.1093/nar/gkq166).
Hiyama et al., "Telomere and Telomerase in Stem Cells" Br. J. Cancer (2007) vol. 96, pp. 1020-1024 (doi: 10.1038/sj.bjc.6603671).
Karsisiotis et al. "Topological Characterization of Nucleic Acid G-Quadruplexes by UV Absorption and Circular Dichroism" Angewandte Chemie (2011) vol. 50, pp. 10645-10648 (doi:10.1002/anie.201105193).
Le et al., "Calculation of Hydrodynamic Properties for G Quadruplex Nucleic Acid Structures From in Silico Bead Models" Topics in current chemistry (2013) vol. 330, pp. 179-210 (doi: 101007/128_2012_351).
Lim et al., "Coexistence of Two Distinct G-Quadruplex Conformations in the hTERT Promoter" Journal of the American Chemical Society (2010) vol. 132, pp. 12331-12342 (doi: 10.1021/ja101252n).
Micheli et al., "Self-Organization of G-Quadruplex Structures in the hTERT Core Promoter Stabilized by Polyaminic Side Chain Perylene Derivatives" Biophysical Chemistry (2010) vol. 153, pp. 43-53 (https://doi.org/10.1016/jbpc.2010.10.003).

(Continued)

*Primary Examiner* — Amy H Bowman
(74) *Attorney, Agent, or Firm* — ALGM LLP; Harry J. Guttman

(57) ABSTRACT

Quadruplex-forming guanine-rich nucleic acid sequences are useful in compositions and methods for inhibiting cellular growth and proliferation and inducing cell death. Compositions for treating a patient are provided, including (i) a safe and effective amount of a sequence having at least 80% nucleic acid identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, SEQ ID NO:12 and combinations thereof, and (ii) a carrier, wherein the isolated oligonucleotide forms at least one quadruplex.

21 Claims, 9 Drawing Sheets

Specification includes a Sequence Listing.

(56) References Cited

OTHER PUBLICATIONS

Murakami et al. "Cell Cycle Regulation, Oncogens, and Antineoplastic Drugs" at Chapter 1 in the Molecular Basis of Cancer, Editors Mendelsohn and Israel, (1995) W B Saunders, Philadelphia, USA.

National Cancer Institute at the National Institutes of Health, "A to Z List of Cancer Drugs," available at http://www.cancer.gov/cancertopics/druginfo/alphalist (last accessed Dec. 20, 2017).

Nygren et al., "The Interactions Between the Fluorescent Dye Thiazole Orange and DNA" Biopolymers (1998) vol. 46, pp. 39-51 (doi: 10.1002/(SICI)1097-0282(199807)46:1<39::AID-BIP4>3.0.CO;2-Z).

Palumbo et al., "Formation of a unique end-to-end stacked pair of G-quadruplexes in the hTERT core promoter with implications for inhibition of telomerase by G-quadruplex-interactive ligands" Journal of the American Chemical Society (2009) vol. 131, pp. 10878-10891 (doi: 10.1021/ja902281d).

Petraccone et al., "The Tail of The Telomere" Journal of the American Chemical Society (2008) vol. 130, pp. 16530-16532 (doi: 10.1021/ja8075567).

Schuck, P. "Size-Distribution Analysis of Macromolecules by Sedimentation Velocity Ultracentrifugation and Lamm Equation Modeling" Biophysical Journal (2000) vol. 78, pp. 1606-1619 (https://doi.org/10.1016/S0006-3495(00)76713-0).

Shay et al., "A Survey of Telomerase Activity in Human Cancer" Eur. J. Cancer (1997) vol. 33, pp. 787-791 (doi: 10.1016/S0959-8049(97)00062-2).

Veldman et al., "Transcriptional Activation of the Telomerase hTERT Gene by Human Papillomavirus Type 16 E6 Oncoprotein" J. Virol (2001) vol. 75, pp. 4467-4472 (doi: 10.1128/JVI.75.9.4467-4472.2001).

Vieregg et al., "Selective Nucleic Acid Capture with Shielded Covalent Probes" Journal of the American Chemical Society (2013) vol. 135, pp. 9691-9699 (doi: 10.1021/ja4009216).

Xing et al., "BRAF V600E and TERT Promoter Mutations Cooperatively Identify the Most Aggressive Papillary Thyroid Cancer with Highest Recurrence" Journal of Clinical Oncology (2014) vol. 32, pp. 2718-2726 (doi: 10.1200/JCO.2014.55.5094).

Biosynthesis "Long DNA Oligonucleotide Synthesis" «https://www.biosyn.com/long-dna-oligonucleotide-synthesis.aspx», 3 pages. (last accessed Dec. 11, 2018).

Biolegio "Long oligo synthesis" «https://www.biolegio.com/products-services/long-oligosi» 2 pages. (last accessed Jan. 13, 2019).

Bioneer "Extendamers from Bioneer" «https://us.bioneer.com/products/Oligonucleotides/ExtendamersLongoligonucleotidesoverview.aspx » 1 page. (last accessed Jan. 13, 2019).

Bozdech et al., (2003) "Expression profiling of the schizont and trophozoite stages of Plasmodium falciparum with a long-oligonucleotide microarray" Genome Biology, vol. 4, No. 2, Article R9. (15 pages).

Eurofins "Extremer" «https://www.eurofinsgenomics.com/en/products/dnarna-synthesis/extremers.aspx» 3 pages. (last accessed Jan. 13, 2019).

Gnirke et al., (2009) "Solution Hybrid Selection with Ultra-long Oligonucleotides for Massively Parallel Targeted Sequencing" Nat Biotechnol., vol. 27, No. 2, pp. 182-189.

IDT "Ultramer DNA Oligonucleotides" «https://www.idtdna.com/pp./products/custom-dna-rna/dna-oligos/ultramer-dna-oligos» 2 pages. (last accessed Jan. 13, 2019).

Khazaei et al., (2016) "Microarray-based long oligonucleotides probe designed for Brucella Spp. detection and identification of antibiotic susceptibility pattern" Electronic Physician, vol. 8, No. 4, pp. 2297-2303.

Sigma Aldrich "Long Oligos" «https://www.sigmaaldrich.com/technical-documents/articles/biology/custom-dna-long-oligos.html» 1 page. (last accessed Jan. 13, 2019).

Wang et al., (2011) "Synthetic long oligonucleotides to generate artificial templates for use as positive controls in molecular assays: drug resistance mutations in influenza virus as an example" Virology Journal, vol. 8, Article 405. (7 pages).

* cited by examiner

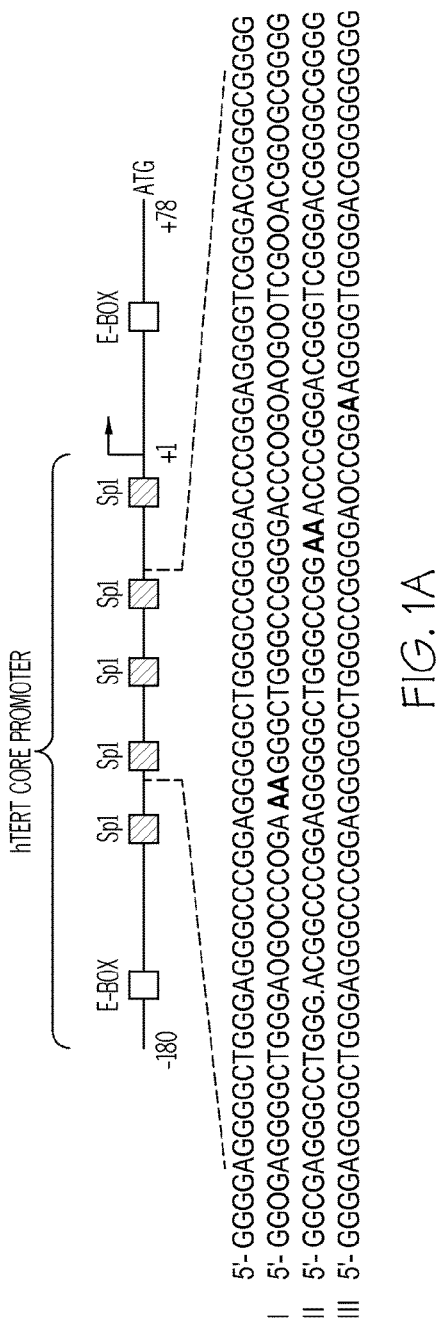
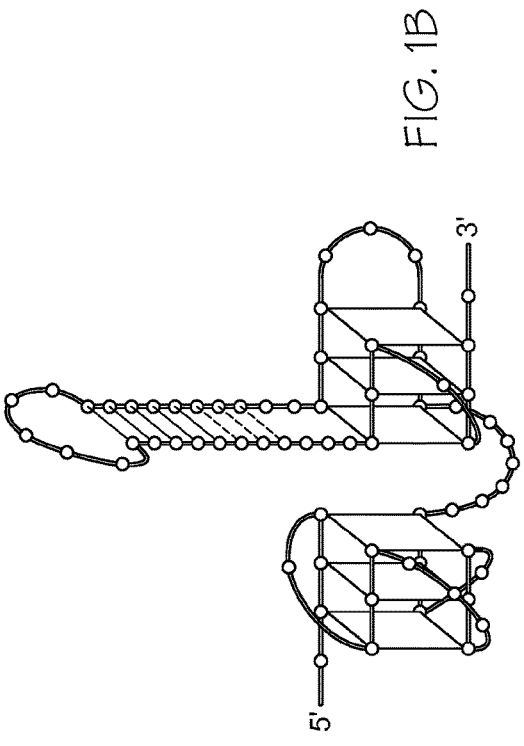
FIG. 1A
FIG. 1B

SEQUENCE LISTING

<160> NUMBER OF SEQ ID NOS: 12

<210> SEQ ID NO 1
<211> LENGTH: 68
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide
      sequence of hTERT

<400> SEQUENCE: 1

```
ggggagggggc tgggagggcc cggaggggggc tgggccgggg acccgggagg ggtcgggacg      60
gggcgggg                                                                  68

<210> SEQ ID NO 2
<211> LENGTH: 68
<212> TYPE: DNA
<213> ORGANISM: homo sapiens
<220> FEATURE:
<221> NAME/KEY: misc_feature
<223> OTHER INFORMATION: Guanosine-rich promoter gene oligonucleotide
      sequence of hTERT-2M

<400> SEQUENCE: 2 ggggagggggc tgggagggcc cggaaagggc tgggccgggg acccgggagg ggtcgggacg      60
gggcgggg                                                                  68

<210> SEQ ID NO 3
<211> LENGTH: 68
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide
      sequence of hTERT+2E

<400> SEQUENCE: 3 ggggagggggc tgggagggcc cggaggggggc tgggccggaa acccgggagg ggtcgggacg      60
gggcgggg                                                                  68

<210> SEQ ID NO 4
<211> LENGTH: 68
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide
      sequence of hTERT+1

<400> SEQUENCE: 4 ggggagggggc tgggagggcc cggaggggggc tgggccggaa acccggaagg ggtcgggacg      60
gggcgggg                                                                  68

<210> SEQ ID NO 5
<211> LENGTH: 19
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide
      sequence of hTERTMM

<400> SEQUENCE: 5
gggaggggtc gggacgggg                                                     19

<210> SEQ ID NO 6
<211> LENGTH: 21
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide
      seqence of hTERT4/6

<400> SEQUENCE: 6
ggggacccgg gaggggtcgg g                                                  21
```

<210> SEQ ID NO 7
<211> LENGTH: 23
<212> TYPE: DNA
<213> ORGANISM: Homo sapiens
<220> FEATURE:
<221> NAME/KEY: misc_feature
<223> OTHER INFORMATION: Guanosine-rich promotor gene oligonucleotide
      sequence of hTERT3

<400> SEQUENCE: 7
gggggctggg ccggggaccc ggg                                         23

<210> SEQ ID NO 8
<211> LENGTH: 19
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide
      sequence of shTERT+1

<400> SEQUENCE: 8 ggaagggggtc gggacgggg                                             19

<210> SEQ ID NO 9
<211> LENGTH: 21
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide
      sequence of shTERT+2M

<400> SEQUENCE: 9
ggaaacccgg gaggggtcgg g                                           21

<210> SEQ ID NO 10
<211> LENGTH: 21
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide
      sequence of MshTERT+1

<400> SEQUENCE: 10
ggggacccgg aaggggtcgg g                                           21

<210> SEQ ID NO 11
<211> LENGTH: 23
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide
      sequence of Mut+2M

<400> SEQUENCE: 11
aagggctggg ccggggaccc ggg                                         23

<210> SEQ ID NO 12
<211> LENGTH: 23
<212> TYPE: DNA
<213> ORGANISM: Homo sapiens
<220> FEATURE:
<221> NAME/KEY: misc_feature
<223> OTHER INFORMATION: Guanosine-rich promoter gene oligonucleotide

```
      sequence of Mut+2E
<400> SEQUENCE: 12 ggggggctggg ccggaaaccc ggg                                            23
```

US 10,370,665 B2

COMPOSITIONS AND METHODS FOR TREATING CANCER, INHIBITING CELL PROLIFERATION, AND INDUCING CELL DEATH

RELATED APPLICATION

This application claims priority under 35 U.S.C. § 119(e) to U.S. Provisional Application Ser. No. 61/947,752, filed Mar. 4, 2014, which application is hereby incorporated by reference in its entirety.

TECHNICAL FIELD

The presently disclosed subject matter relates to methods and compositions for inhibiting cell proliferation and growth and inducing cell death comprising the administration of compositions comprising quadruplex-forming guanosine-rich promoter gene oligonucleotides (GPGOs) and their derivatives.

BACKGROUND OF THE INVENTION

Guanine-rich nucleic acid sequences are capable of forming quadruplex, or four-stranded, conformations. These quadruplex structures are comprised of a series of quartets of hydrogen-bonded guanines, which together create a roughly cubical structure. Many cancer-related genes have quadruplex forming sequences in their G-rich promoter regions, including hTERT.

G-rich quadruplex forming genomic sequences provide an important target for methods and compositions that inhibit cell proliferation and induce cell death. The need exists to develop therapeutic methods and compositions comprising G-rich quadruplex forming oligonucleotides.

SUMMARY

G-rich quadruplex forming oligonucleotides are useful in inhibiting cellular growth and proliferation, treating cancer, and inhibiting telomerase activity. Accordingly, it is an object of the present invention to provide a composition for treating a patient, comprising (i) a safe and effective amount of at least one isolated oligonucleotide comprising a sequence having at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, SEQ ID NO:12, and combinations thereof, and (ii) a carrier, wherein the isolated oligonucleotide forms at least one quadruplex.

In another embodiment, a composition for treating a patient is provided, comprising at least two isolated oligonucleotides, each oligonucleotide comprising a sequence having at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, and SEQ ID NO:12 and (ii) a carrier, wherein the isolated oligonucleotide forms at least one quadruplex.

In another embodiment, a composition for treating a patient is provided, comprising at least three isolated oligonucleotides, each oligonucleotide comprising a sequence having at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, and SEQ ID NO:12 and (ii) a carrier, wherein the isolated oligonucleotide forms at least one quadruplex.

In another embodiment, a method of treating cancer is provided, comprising administering to a patient in need thereof a composition comprising (i) a safe and effective amount of an oligonucleotide having at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, and SEQ ID NO:12 and combinations thereof, and (ii) a carrier, wherein the oligonucleotide forms at least one quadruplex.

In another embodiment, a method of inhibiting cell growth is provided, comprising contacting the cell with a composition comprising (i) a safe and effective amount of an oligonucleotide having at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, and SEQ ID NO:12 and combinations thereof, and (ii) a carrier, wherein the oligonucleotide forms at least one quadruplex.

In still another embodiment, a method of inhibiting telomerase activity of a cell is provided, comprising contacting the cell with a composition comprising (i) a safe and effective amount of an oligonucleotide having at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, and SEQ ID NO:12 and combinations thereof, and (ii) a carrier, wherein the oligonucleotide forms at least one quadruplex.

In another embodiment, a method of treating a patient having a tumor is provided, the method comprising (a) performing a biopsy of the patient's tumor; (b) determining a gene expression profile of the tumor; (c) identifying one or more genes that are overexpressed in the tumor, based on the gene expression profile of step (b); (d) selecting one or more guanosine-rich promoter gene oligonucleotide (GPGO) sequences corresponding to the overexpressed genes identified in step (c); (e) administering to the patient a composition comprising a safe and effective amount of the one or more GPGO sequences of step (d), wherein the one or more GPGO sequences have at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, and SEQ ID NO:12 and combinations thereof, and wherein each of the one or more GPGO sequences forms at least one quadruplex.

These and other objects, features, embodiments, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified.

BRIEF DESCRIPTION OF THE DRAWINGS

FIG. 1. The hTERT promoter sequence and proposed structure. FIG. 1 (top) depicts the sequence of the hTERT core promoter and mutated sequences of the hTERT promoter observed in melanomas. For the mutated sequences of the hTERT promoter, I=hTERT-2M, II=hTERT+2E, and III=hTERT+1. FIG. 1 (bottom) depicts previously proposed structure of the hTERT core promoter.

FIG. 2. Circular dichroism studies of hTERT and mutant sequences.

FIG. 6. Structure and Stability of hTERT promoter oligonucleotides encoding wild type and mutated sequences.

FIG. 7 demonstrates that oligonucleotides encoding the entire WT quadruplex forming sequence (67 bp in length) and a shorter WT oligonucleotide (21 bp) bind to the parent sequence (lanes 1 and 3). This binding can be competed by cold oligonucleotide (lane 2 and 4) indicating that the binding is sequence specific. In lanes 5 and 6, a similar experiment is performed with an oligonucleotide containing one of the melanoma mutations binding to a mutated parent sequence. For the mutated sequence of the hTERT promoter, Mu1=Mut+2M.

FIG. 8 depicts the telomere promoter quadruplex-forming oligonucleotides (WT and three mutant sequences) inhibited the proliferation of cell lines with mutated promoter sequences to a greater extent than those with a wild type hTERT promoter, suggesting that stabilization of the quadruplex structure in the hTERT promoter results in decreased expression and telomerase activity. For the mutated sequences of the hTERT promoter, Mu1=hTERT-2M, Mu2=hTERT+2E, and Mu3=shTERT+1.

FIG. 9 depicts the results of using reporter vectors in which luciferase is expressed under the control of the wild type hTERT promoter sequence. The results demonstrate that oligonucleotides comprised of the wild type hTERT quadruplex-forming sequence can inhibit promoter activity.

DETAILED DESCRIPTION

Figure 2A:
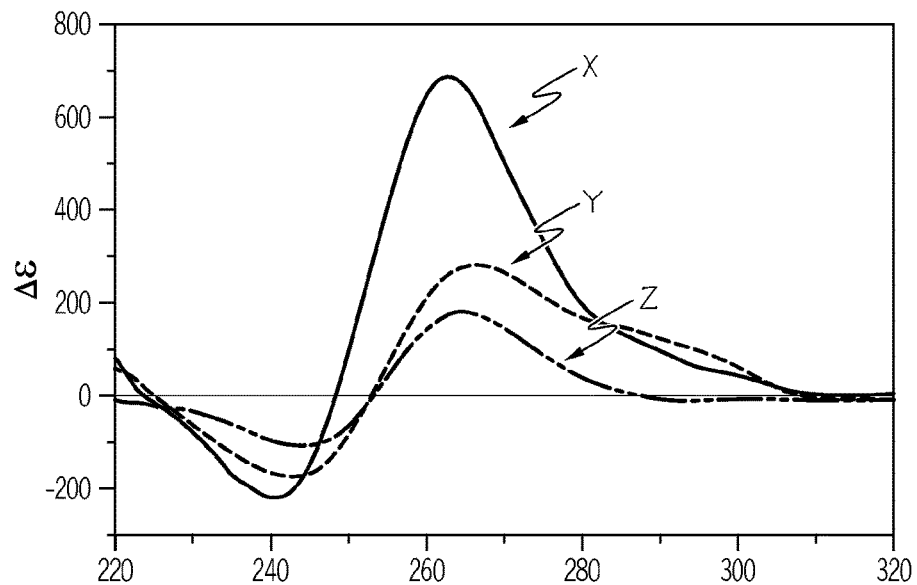
FIG. 2(A) depicts the molar circular dichroism (Δε) of the hTERT promoter sequence in solution (X). The spectrum predicted for the structure shown in FIG. 1 is depicted as (Y). The experimentally observed spectrum for the parallel quadruplex structure formed by the c-myc promoter sequence variant 1XAV is shown as (Z).

The following terms are used in the present application:

The term "patient," as used herein, refers to any mammalian subject, including humans.

The term "safe and effective amount" refers to an amount of a composition high enough to significantly positively modify the symptoms and/or condition to be treated, such as by inhibiting or reducing the proliferation of, or inducing cell death (for example, by inducing apoptosis) of dysplastic, hyperproliferative, or malignant cells, but low enough to avoid serious side effects (at a reasonable risk/benefit ratio), within the scope of sound medical judgment. The safe and effective amount of oligonucleotides for use in the compositions and methods of the invention herein will vary with the particular condition being treated, the age and physical condition of the patient to be treated, the severity of the condition, the duration of the treatment, the nature of concurrent therapy, the particular oligonucleotide(s) being employed, the particular pharmaceutically-acceptable carriers utilized, and like factors within the knowledge and expertise of the attending physician.

As used herein, the term "oligonucleotide" refers to a molecule comprising two or more deoxyribonucleotides or ribonucleotides. The exact size depends on a number of factors including the specificity and binding affinity to target ligands. In referring to "bases" or "nucleotides," the terms include both deoxyribonucleic acids and ribonucleic acids.

The terms "guanosine-rich promoter gene oligonucleotide," "G-rich promoter gene oligonucleotide," or "GPGO," as used herein, refer to oligonucleotides that include the G-rich promoter sequences of the gene human telomerase reverse transcriptase ("hTERT"), which form at least one quadruplex, and any oligonucleotide which includes a sequence having at least 80% nucleic acid sequence identity with the G-rich promoter sequence of the gene hTERT, and which forms at least one quadruplex. Quadruplex formation may be determined by circular dichroism spectroscopy (see, for example, FIG. 2). In one embodiment, a GPGO includes a sequence having at least 85%, 90%, 95%, 96%, 97%, 98%, 99%, or essentially 100% nucleic acid sequence identity with the G-rich promoter sequence of hTERT. In certain embodiments, a GPGO includes a sequence having at least 80%, 85%, 90%, 95%, 96%, 97%, 98%, 99%, or essentially 100% nucleic acid sequence identity with the full length G-rich promoter sequence of hTERT, while in other embodiments a GPGO includes a sequence having at least 80%, 85%, 90%, 95%, 96%, 97%, 98%, 99%, or essentially 100% nucleic acid sequence identity with a partial G-rich promoter sequence of hTERT. In another embodiment, a GPGO includes a sequence having at least 80%, 85%, 90%, 95%, 96%, 97%, 98%, 99%, or essentially 100% nucleic acid sequence identity with the G-rich promoter sequence of a mutated hTERT promoter. The reported hTERT promoter mutations are shown in FIG. 1. In certain embodiments, a GPGO includes a sequence having at least 80%, 85%, 90%, 95%, 96%, 97%, 98%, 99%, or essentially 100% nucleic acid sequence identity with a full length G-rich promoter sequence of a mutated hTERT promoter, while in other embodiments, a GPGO includes a sequence having at least 80%, 85%, 90%, 95%, 96%, 97%, 98%, 99%, or essentially 100% nucleic acid sequence identity with a partial G-rich promoter sequence of the mutated hTERT promoter. In specific embodiments, the GPGO includes the sequences listed in Table 1.

The term "quadruplex," as used herein, refers to nucleic acid sequences capable of forming four-stranded conformations. These quadruplex structures are comprised of a series of quartets of hydrogen-bonded guanines, which together create a roughly cubical structure. Many cancer-related genes have quadruplex forming sequences in their G-rich promoter regions. These genes include, but are not limited to, the hTERT, c-Myc, c-Myb, VEGF, RET, PDGF-A, Bcl-2, c-Kit, BCL-1, K-ras, Rb and HIF1-α genes.

"Percent (%) nucleic acid sequence identity" with respect to sequences identified herein is defined as the percentage of nucleotides in a candidate sequence that are identical with the nucleotides in the sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software.

The term "carrier," as used herein, includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The terms "treat," "treatment," and "treating," as used herein, refer to a method of alleviating or abrogating a disease, disorder, and/or symptoms thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhone-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone. Suitable chemotherapeutic agents are listed by the National Cancer Institute at the National Institutes of Health, "A to Z List of Cancer Drugs," available at http://www.cancer.gov/cancertopics/druginfo/alphalist (last accessed Mar. 2, 2015), incorporated herein by reference in its entirety.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1-arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogens, and antineoplastic drugs" by Murakami et al. (W B Saunders: Philadelphia, 1995), especially p. 13. Also included in the term "growth inhibitory agent" are chemotherapeutic agents.

The terms "inhibiting cell development" or "inhibiting cell growth" refer to inhibiting growth of a cell, especially a cancer cell overexpressing any of the genes identified herein, either in vitro or in vivo. Inhibiting cell growth or cell development includes blocking cell cycle progression (at a place other than S phase), for example, G1-arrest or M-phase arrest.

The term "gene expression profile," as used herein, refers to the measurement of the activity of multiple genes at once to create a global picture of cellular function.

The term "overexpress" or "overexpressed" as used herein, refer to a gene product which is expressed at levels greater than normal endogenous expression for that gene product.

The isolated oligonucleotides of the present invention, GPGOs, are rich in guanosine and are capable of forming quadruplexes, or G-quartet structures. Specifically, the oligonucleotides of the present invention are primarily comprised of thymidine and guanosine with at least one contiguous guanosine repeat in the sequence of each oligonucleotide. The G-rich oligonucleotides are stable and can remain undegraded in serum for prolonged periods of time and retain their growth inhibiting effects.

The novel oligonucleotides of the present invention, GPGOs, can be used to inhibit the proliferation of, or induce cell death in, malignant, dysplastic and/or hyperproliferative cells. Table 1 provides the sequences of GPGOs useful in the compositions and methods of the present invention.

TABLE 1

GPGO Sequences (Bolded nucleotides represent mutated sequences)

hTERT WT

SEQ ID NO: 1

SEQ 5' GGGGAGGGGCTGGGAGGGCCCGGAGGGGGCTGGGCCGGGGAC
CCGGGAGGGGTCGGGACGGGGCGGGG 3' hTERT - 2M

SEQ ID NO: 2

SEQ 5' GGGGAGGGGCTGGGAGGGCCCGGAAAGGGCTGGGCCGGGGAC
CCGGGAGGGGTCGGGACGGGGCGGGG 3' hTERT + 2E

SEQ ID NO: 3

SEQ 5' GGGGAGGGGCTGGGAGGGCCCGGAGGGGGCTGGGCCGGAAAC
CCGGGAGGGGTCGGGACGGGGCGGGG 3' hTERT + 1

SEQ ID NO: 4

SEQ 5' GGGGAGGGGCTGGGAGGGCCCGGAGGGGGCTGGGCCGGAAAC
CCGGAAGGGGTCGGGACGGGGCGGGG 3' hTERTMM

SEQ ID NO: 5

SEQ 5' GGGAGGGGTCGGGACGGGG 3' hTERT4/6

SEQ ID NO: 6

SEQ 5' GGGGACCCGGGAGGGGTCGGG 3' hTERT3

SEQ ID NO: 7

SEQ 5' GGGGGCTGGGCCGGGGACCCGGG 3' shTERT + 1

SEQ ID NO: 8

SEQ 5' GGAAGGGGTCGGGACGGGG 3' shTERT + 2M

SEQ ID NO: 9

SEQ 5' GGAAACCCGGGAGGGGTCGGG 3'

MshTERT + 1

SEQ ID NO: 10

SEQ 5' GGGGACCCGGAAGGGGTCGGG 3'

Mut + 2M

SEQ ID NO: 11

SEQ 5' AAGGGCTGGGCCGGGGACCCGGG 3'

Mut + 2E

SEQ ID NO: 12

SEQ 5' GGGGGCTGGGCCGGAAACCCGGG 3'

The oligonucleotides can be modified at their 3' end in order to alter a specific property of the oligonucleotide. For example, the 3'-terminus of the oligonucleotide can be modified by the addition of a propyl amine group which has been found to increase the stability of the oligonucleotide to serum nucleases. Additional example of a 3' modification is the addition of a polyethylene glycol substituent via coupling to an appropriate linker to any of the above sequences. Addition of a polyethylene glycol of different molecular weights, especially between 200 and 20,000 molecular weight, results in modifying the pharmacokinetic parameters associated with the oligonucleotides. Other modifications that are well known in the art include 3' and 5' modifications, for example, the binding of cholesterol, and backbone modifications, for example, phosphorothioate substitution and/or 2'-O-methyl RNA.

Dosage Forms and Administration

The GPGOs of the present invention can be administered to a patient or subject either alone or as part of a pharmaceutical composition. The GPGOs can be administered to patients either orally, rectally, parenterally (intravenously, intramuscularly, or subcutaneously), intracisternally, intravaginally, intraperitonally, intravesically, locally (powders, ointments, or drops), or as a buccal or nasal spray.

Compositions of the GPGOs of the present invention suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active ingredient (GPGO) is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a GPGO of the present invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

In addition, the oligonucleotides of the present invention can exist in unsolvated as well as solvated forms with pharmaceutically acceptable solvents such as water, ethanol, and the like. In general, the solvated forms are considered equivalent to the unsolvated forms for the purposes of the present invention.

The GPGOs of the present invention can be administered to a patient at dosage levels in the range of about 1.5 mg to about 150 mg per day; it is also possible to administer larger amounts, such as from about 150 mg to 1 g per day. A unit dosage form of GPGOs is an amount which would be administered as a single dose. For a normal human adult having a body weight of about 70 kilograms, a dosage in the range of about 0.2 mg to about 2.0 mg per kilogram of body weight per day is preferable. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art. The GPGOs of the present invention can be given in single and/or multiple dosages.

In addition, it is intended that the present invention cover GPGOs made either using standard organic synthetic techniques, including combinatorial chemistry or by biological methods, such as through metabolism.

The GPGOs of the present invention may also be used in combination with other chemotherapeutic agents to provide a synergistic or enhanced efficacy or inhibition of neoplastic cell growth. For example, the GPGOs of the present invention can be administered in combination with chemotherapeutic agents including, for example, cis-platin, mitoxantrone, etoposide, camptothecin, 5-fluorouracil, vinblastine, paclitaxel, docetaxel, mithramycin A, dexamethasone, caffeine, and other chemotherapeutic agents and/or growth inhibitory agents well known to those skilled in the art.

In one embodiment of the invention, a composition for treating a patient is provided, comprising (i) a safe and effective amount of at least one oligonucleotide comprising a sequence having at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, SEQ ID NO:12 and combinations thereof, and (ii) a carrier, wherein the oligonucleotide forms at least one quadruplex.

In another embodiment, a composition for treating a patient is provided, comprising (i) a safe and effective amount of at least two oligonucleotides, each oligonucleotide comprising a sequence having at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, and SEQ ID NO:12 and (ii) a carrier, wherein each of said oligonucleotides forms at least one quadruplex.

In another embodiment, a composition for treating a patient is provided, comprising (i) a safe and effective amount of at least three oligonucleotides, each oligonucleotide comprising a sequence having at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, and SEQ ID NO:12 and (ii) a carrier, wherein each of said oligonucleotides forms at least one quadruplex.

In one embodiment, any of the above compositions comprises one or more sequences having at least 85%, 90%, 95%, 96%, 97%, 98%, 99%, or essentially 100% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, and SEQ ID NO:12.

In another embodiment, any of the above compositions comprise one or more sequences selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, SEQ ID NO:12, and combinations thereof.

In another embodiment, any of the above compositions of the present invention further comprises a chemotherapeutic agent. Suitable chemotherapeutic agents include, but are not limited to, adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhone-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also suitable are hormonal agents that act to regulate or inhibit hormone action on tumors such as tamoxifen and onapristone.

In another embodiment, any of the above compositions of the present invention further comprises a growth inhibiting agent. Suitable growth inhibitory agents include, but are not limited to, the vincas (vincristine and vinblastine); taxol; topo II inhibitors such as doxorubicin, epirubicin, daunorubicin, etoposide, and bleomycin; DNA alkylating agents such as tamoxifen, prednisone, dacarbazine, mechlorethamine, cisplatin, methotrexate, 5-fluorouracil, and cytosine arabinoside ("Ara-C"). Also included in the term "growth inhibitory agent" are chemotherapeutic agents.

In another embodiment, a method of treating cancer is provided, comprising administering to a patient in need thereof a composition comprising (i) a safe and effective amount of at least one oligonucleotide comprising a sequence having at least 80% nucleic acid sequence identity with a sequence selected from the group consisting of SEQ ID NOS: 1-12, and combinations thereof, and (ii) a carrier, wherein the oligonucleotide forms at least one quadruplex. In another embodiment, the composition of the method comprises a safe and effective amount of two oligonucleotides, each oligonucleotide comprising a sequence having at least 80% nucleic acid sequence identity with a sequence selected from the group consisting of SEQ ID NOS: 1-12, wherein each of said oligonucleotides forms at least one quadruplex. In another embodiment, the composition of the method comprises a safe and effective amount of three oligonucleotides, each oligonucleotide comprising a sequence having at least 80% nucleic acid sequence identity with a sequence selected from the group consisting of SEQ ID NOS: 1-12, wherein each of said oligonucleotides forms at least one quadruplex. The composition of the method can be administered to the patient in a variety of modes, including but not limited to, orally, rectally, parenterally, intracistemally, intravaginally, intraperitoneally, intravesically, locally, or as a buccal or nasal spray. In a specific embodiment, the type of cancer to be treated includes, but is not limited to, leukemia, lymphoma, brain cancer, breast cancer, lung cancer, pancreatic cancer, colon cancer, ovarian cancer, liver cancer, prostate cancer, bone cancer, gastro-intestinal cancer, ocular cancer, head and neck cancer, and melanoma.

In another embodiment, a method of inhibiting cell growth is provided, comprising contacting a cell with a composition comprising (i) an effective amount or a safe and effective amount of at least one oligonucleotide comprising a sequence having at least 80% nucleic acid sequence identity with a sequence selected from the group consisting of SEQ ID NOS: 1-12, and combinations thereof, and (ii) a carrier, wherein the oligonucleotide forms at least one quadruplex. In another embodiment, the composition of the method comprises an effective amount or a safe and effective amount of two oligonucleotides, each oligonucleotide comprising a sequence having at least 80% nucleic acid sequence identity with a sequence selected from the group consisting of SEQ ID NOS: 1-12, wherein each of said oligonucleotides forms at least one quadruplex. In another embodiment, the composition of the method comprises an effective amount or a safe and effective amount of three oligonucleotides, each oligonucleotide comprising a sequence having at least 80% nucleic acid sequence identity with a sequence selected from the group consisting of SEQ ID NOS: 1-12, wherein each of said oligonucleotides forms at least one quadruplex. In one embodiment, the composition of the method may be administered in vivo, to a subject, or in vitro, to cells. In a specific embodiment, the composition is administered to a patient. The composition of the method can be administered to the patient in a variety of modes, including but not limited to, orally, rectally, parenterally, intracistemally, intravaginally, intraperitoneally, intravesically, locally, or as a buccal or nasal spray.

In a further embodiment, a method of inhibiting telomerase activity of a cell is provided, comprising contacting the cell with a composition comprising (i) an effective amount or a safe and effective amount of at least one oligonucleotide comprising a sequence having at least 80% nucleic acid sequence identity with a sequence selected from the group consisting of SEQ ID NOS: 1-12, and combinations thereof, and (ii) a carrier, wherein the oligonucleotide forms at least one quadruplex. In another embodiment, the composition of the method comprises an effective amount or a safe and effective amount of two oligonucleotides, each oligonucleotide comprising a sequence having at least 80% nucleic acid sequence identity with a sequence selected from the group consisting of SEQ ID NOS: 1-12, wherein each of said oligonucleotides forms at least one quadruplex. In another embodiment, the composition of the method comprises a safe and effective amount of three oligonucleotides, each oligonucleotide comprising a sequence having at least 80% nucleic acid sequence identity with a sequence selected from the group consisting of SEQ ID NOS: 1-12, wherein each of said oligonucleotides forms at least one quadruplex. In one embodiment, the composition of the method may be administered in vivo, to a subject, or in vitro, to cells. In a specific embodiment, the composition is administered to a patient. The composition of the method can be administered to the patient in a variety of modes, including but not limited to, orally, rectally, parenterally, intracistemally, intravaginally, intraperitoneally, intravesically, locally, or as a buccal or nasal spray.

In another embodiment, a method for treating a patient having a tumor is provided, the method comprising: comprising: (a) performing a biopsy of the patient's tumor; (b) determining a gene expression profile of the tumor; (c) identifying one or more genes that are overexpressed in the tumor, based on the gene expression profile of step (b); (d) selecting one or more guanosine-rich promoter gene oligonucleotide (GPGO) sequences corresponding to the overexpressed genes identified in step (c); (e) administering to the patient a composition comprising a safe and effective amount of the one or more GPGO sequences of step (d), wherein the one or more GPGO sequences have at least 80% nucleic acid sequence identity with a sequence selected from the group consisting of SEQ ID NO: 1, SEQ ID NO: 2, SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, SEQ ID NO:12, and combinations thereof, and wherein each of the one or more GPGO sequences forms at least one quadruplex. In more specific embodiments, the overexpressed gene identified is step (c) is hTERT.

EXAMPLES

The following examples are given by way of illustration and are in no way intended to limit the scope of the present invention.

Example 1

An Improved Model for the hTERT Promoter Quadruplex Materials and Methods

Oligodeoxynucleotides.

Names, sequences and absorption coefficients of the oligonucleotides used in this study are given in Table I. hTERT (obtained from Oligos Etc.) was dissolved in water at a concentration of 650 μM. 1XAV was from IDT, Coralville, Iowa The lyophilized, desalted powder was dissolved in 10 mM LiPO$_4$, pH 7.0 at a concentration of 2 mM. The stock solutions of both oligonucleotides were stored at 4° C. Solutions for fluorescence polarization studies were prepared at ~1 μM concentration in 10 mM tetrabutyl ammonium phosphate, 1 mM EDTA, 200 mM KCl, pH 7.0 (referred to hereafter as tBAP folding buffer), denatured at 90° C. in a water bath for 10-15 min, followed by annealing by slowly cooling to room temperature in the bath. Folding to the quadruplex state was checked by recording the CD spectrum of the sample over the wavelength range 340 nm to 220 nm and observing a maximum in the CD spectrum at 260 nm and a minimum at 240 nm.

Reagents.

Thiazole orange, whose fluorescence quantum yield increases significantly when bound to DNA[25], was from Sigma Chemical Co. (St. Louis, Mo.). A stock solution of 250 μM dye was prepared in folding buffer containing 200 mM KCl and 20% sucrose. The final concentrations of the dye and oligonucleotide in the fluorescence polarization experiments was estimated by spectrophotometry with a Jasco V-550 instrument in conjunction with the appropriate absorption coefficient for the DNA along with a value of $\varepsilon_{500\ nm}$ of 63 mM$^{-1}$ cm$^{-1}$ for the dye. To ensure a negligible concentration of free dye, polarization experiments were carried out with excess DNA (DNA:dye≈3:1).

KCl, tetrabutylammonium dihydrogen phosphate, tetrabutylammonium hydroxide and EDTA (acid form) were from Sigma. Sucrose was from Mallinckrodt Chemicals, Phillipsburg, N.J., and LiH$_2$PO$_4$ and LiOH monohydrate were from Aldrich Chemicals, Milwaukee, Wis.

TABLE 1

Oligodeoxynucleotides used in this study.

| Name | Sequence | MW | $\varepsilon_{260\ nm}$ (mM$^{-1}$ cm$^{-1}$) |
|---|---|---|---|
| hTERT | 5'-GGG GAG GGG CTG GGA GGG CCC GGA GGG GGC TGG GCC GGG GAC CCG GGA GGG GTC GGG ACG GGG CGG GG-3' | 21632.8 | 659.3 |
| 1XAV | 5'-TGA GGG TGG GTA GGG TGG GTA A-3' | 6991.6 | 228.7 |

Circular Dichroism and Thermal Denaturation.

Thermal denaturation of quadruplexes was monitored using a Jasco J-810 spectropolarimeter (Jasco Inc., Easton, Md.) equipped with a programmable Peltier thermostatted cell holder and a magnetic stirrer. CD spectra were collected using instrumental parameters: 280<λ<350 nm, 1.0 nm step size, 200 nm/min scan rate, 1.0 nm bandwidth, 2 s integration time, with 4 total scans averaged. For melting experiments, samples at 3-4 μM in a 1-cm path length cuvette were equilibrated in the cuvette holder at 4° C. prior to starting the melt. Melting experiments were carried out with the thermal parameters: 4° C./min ramp, 0.05° C. equilibration with a 60 s delay prior to acquisition. Spectra were corrected by subtracting a solvent blank. Melts were carried out in duplicate on successive days; data presented here are from the second melt. CD data were normalized to molar circular dichroism (Δε) based on DNA strand concentration using equation (1)

$$\Delta\varepsilon = \theta/(32982 * c * l) \quad (1)$$

where θ is the CD ellipticity in millidegrees, c is DNA concentration in mol/L, and l is the path length in cm.

Analytical Ultracentrifugation.

Sedimentation velocity measurements were carried out in a Beckman Coulter ProteomeLab XL-A analytical ultracentrifuge (Beckman Coulter Inc., Brea, Calif.) at 20.0° C. and at 50,000 rpm in standard 2 sector cells. Data (200 scans collected over a 10 hour centrifugation period) were analyzed using the program Sedfit in the continuous c(s) mode or by a model assuming discrete, noninteracting species (www.analyticalultracentrifugation.com). Buffer density was determined on a Mettler/Paar Calculating Density Meter DMA 55A at 20.0° C. and buffer viscosity was measured on an Anton Paar Automated Microviscometer AMVn. For the calculation of frictional ratio, 0.55 mL/g was used for partial specific volume and 0.3 g/g was assumed for the amount of water bound. hTERT sequences were dissolved to give a final concentration of 1 mM in tBAP folding buffer, diluted to give an absorbance at 260 nm of 0.5, heated in a boiling water bath for 10 minutes and allowed to cool to room temperature before centrifugation.

Molecular Dynamics Simulations and HYDROPRO Calculations.

Molecular models of G-quadruplex structures were created using the parallel quadruplex structure 1XAV from the Protein Data Bank with manual modification of the loop regions to for the hTERT sequence. Appropriate coordinating ions were added to the stacked G-tetrads of each model and additional ions were added to neutralize the G-quadruplex structures. The system was solvated in a rectilinear box of TIP3P water molecules with 15 Å buffer. The system was equilibrated using the following protocol: (i) minimize water and ions (1000 steps-500 steepest descents) holding the DNA fixed (50 kcal/mol/Å), (ii) 50 ps MD (heating to 300 K) with 20 ns MD as the production trajectory. A further 10 ns of accelerated MD production trajectory was obtained[26]. Simulations were performed in the isothermal isobaric ensemble (P=1 atm, T=300K) using sander and GPU version of pmemd (AMBER 13). Periodic boundary conditions and Particle-Mesh-Ewald algorithms were used. A 2.0 fs time step was used with bonds involving hydrogen atoms frozen using SHAKE. Analysis of the trajectory was performed using the cpptraj module of the AmberTools 13 Package. Calculations of hydrodynamic properties were done using the program HYDROPRO 10[27] using the recommended quadruplex parameters[28] on 5000 snapshots of the accelerated MD trajectory.

Fluorescence Experiments.

Fluorescence excitation, emission, and polarization spectra were determined with a Jasco FP-6500 fluorescence spectrophotometer equipped with an ADP-303T Peltier temperature controller and an APH-103 fluorescence polarization unit (Jasco, Inc., Easton, Md.). Instrumental settings were: λex=510 nm, λem=530 nm, 5 nm emission and excitation bandwidth, 2 s response time. Excitation and emission spectra were corrected by subtraction of a solvent blank.

Determination of Rotational Relaxation Time.

The rotational relaxation time of a particle is defined as the time required for it to rotate through an angle θ of 68.4° (cos θ=1/e). This time depends on the volume V of the molecule as well as the viscosity η and temperature T of the medium through the relationship $\rho = 3\eta V/RT$. The rotational relaxation time $\rho_0$ for a spherical molecule without bound solvent can be calculated from the relationship $\rho_0 = 3\eta M \bar{v}/RT$, where M is the molecular weight and $\bar{v}$ is the partial specific volume (taken as 0.55 cm$^3$/mol for DNA quadruplexes). The ratio $\rho/\rho_0$ is considered to indicate deviations from a spherical shape and/or hydration of the molecule. The rotational relaxation time as defined above is related to the rotational correlation time $\phi$ (the time required for a molecule to rotate through 1 radian) by the equation $\phi=3\,\rho$[29].

The rotational relaxation time of a fluorescently labelled molecule can be determined by measuring the degree of fluorescence polarization as a function of viscosity of the solution which can be varied by changing the temperature. Rotational relaxation times for the complexes of hTERT-FL and 1XAV with thiazole orange were determined in tBAP folding buffer with 200 mM KCl and 20% (w/v) sucrose at 2° C. intervals over the temperature range 5 to 39° C. The viscosity of the sucrose solution at the experimental temperatures were obtained by interpolation (where necessary) from standard tables[6].

The data sets were analyzed graphically as described by Montanaro and Sperti[30] using the Perrin equation (Eq. 2) which relates the degree of fluorescence polarization P to the rotational relaxation time $\rho$ of the fluorescent particle and $\tau$, the lifetime of the excited state:

$$\frac{1}{P} - \frac{1}{3} = \left(\frac{1}{P_0} - \frac{1}{3}\right)\left(1 + \frac{3\tau}{\rho}\right). \quad (2)$$

P is defined as $(I_{\|}-G\cdot I_{\perp})/(I_{\|}+G\cdot I_{\perp})$, where $I_{\perp}$ is the emission intensity with the excitation polarizer at 90° (vertical orientation) and the emission polarizer is at 0° (horizontal orientation), and $I_{\|}$ is the intensity with both polarizers at 90°. G is a grating correction factor=$i_{\perp}/i_{\|}$ with $i_{\perp}$ indicating the excitation polarizer is at 0° and the emission polarizer is at 90°, and $i_{\|}$ indicating that both polarizers are in the 0° orientation. $P_0$ is the intrinsic polarization. The quantity (1/P−⅓) is plotted vs. T/η and $\rho$ is estimated from the slope and intercept estimated by linear regression.

Determination of Fluorescence Lifetime.

The fluorescence lifetime $\tau$ for the excited state of thiazole orange bound to hTERT and 1XAV was determined with an ISS K2 Multifrequency Phase Fluorometer (ISS, Champaign, Ill.). The sample was excited at room temperature with a 468-nm LED and polarizers set at "magic angle" conditions. Emission was measured through a 520-nm band pass filter (Newport Corp.). The instrument was calibrated with fluorescein in 0.1 M NaOH (lifetime=4.0 ns). Phase and amplitude modulation data were analyzed with the ISS program Vinci Beta 1.7 (ISS) to determine lifetimes.

Figure 2B:
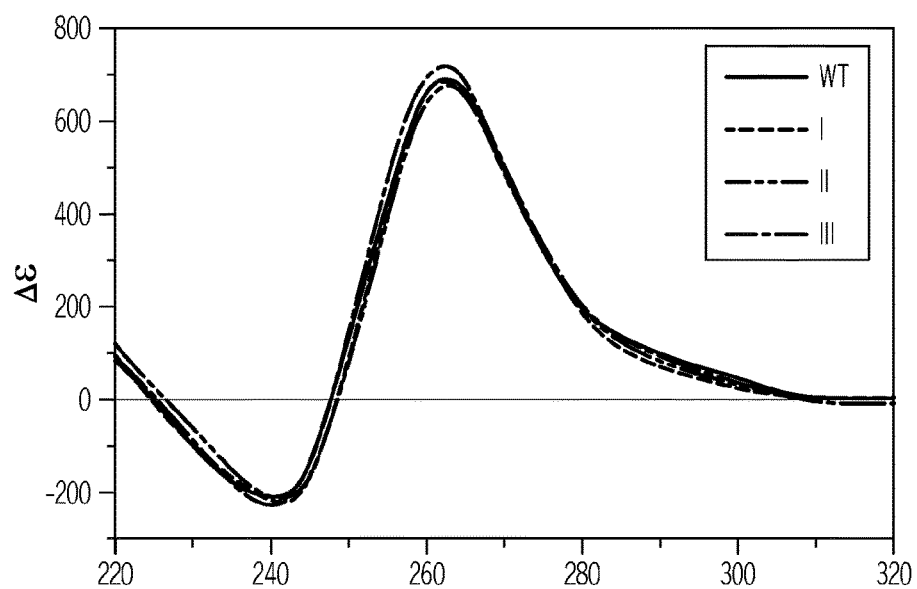
FIG. 2(B) depicts molar circular dichroism of the folded wild-type and mutant sequences shown in FIG. 1. For the mutated sequences of the hTERT promoter, I=hTERT-2M, II=hTERT+2E, and III=hTERT+1.
Figure 3:
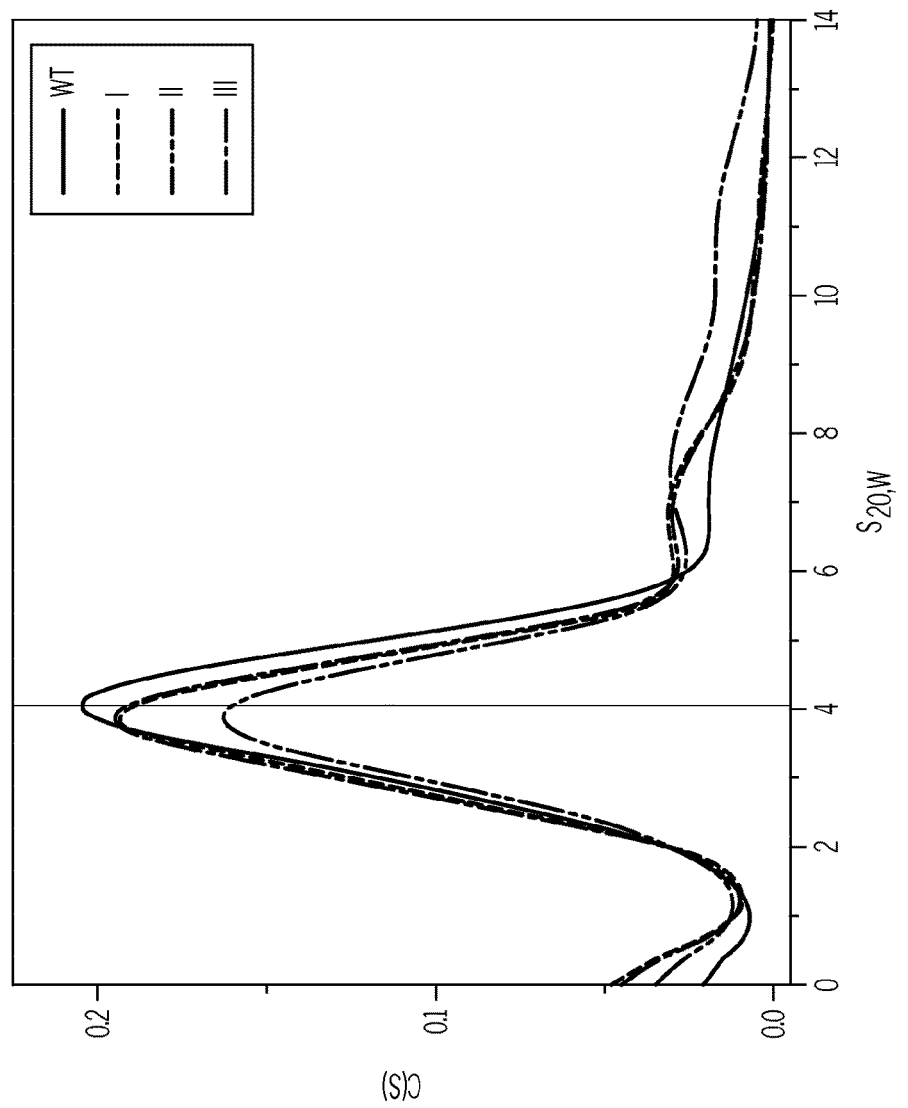
FIG. 3. Results of sedimentation velocity experiments of hTERT promoter sequences in solution. The distribution of sedimentation coefficients, corrected for viscosity and temperature, are shown in FIG. 3, revealing a major species with $S_{20,w}$ of 4.05±0.04 for the folded wild-type sequence. $S_{20,w}$ values for folded mutant sequences are slightly but significantly reduced to 3.5-3.6 $S_{20,w}$. For the mutated sequences of the hTERT promoter, I=hTERT-2M, II=hTERT+2E, and III=hTERT+1.

Results and Discussion a. hTERT Promoter Mutations and Previously Reported Structure The locations of the reported hTERT promoter mutations are shown in FIG. 1, along with the previously proposed structure of the hTERT promoter. In that structure the reported G to A transitions would be somewhat oddly placed with one in the hairpin loop, one in the duplex stem and one in the antiparallel quadruplex. The effects of these transitions on the stability and function of the proposed structure are by no means clear.

b. Circular Dichroism Spectra for the hTERT Promoter and hTERT Promoter Sequences with Reported Mutations FIG. 2 shows circular dichroism (CD) spectra for the folded promoter and sequences containing the reported mutations. For the mutated sequences of the hTERT promoter, I=hTERT-2M, II=hTERT+2E, and III=hTERT+1. For the wild-type sequence, the observed CD spectrum is characteristic of a parallel quadruplex structure (Karsisiotis, A. I. et al. Topological characterization of nucleic acid G-quadruplexes by UV absorption and circular dichroism. *Angewandte Chemie* 50, 10645-10648, doi:10.1002/anie.201105193 (2011)), and is notable for the exceptionally high amplitude of its molar circular dichroism. The observed spectrum is inconsistent with what would be expected for the proposed structure by Palumbo et. Al, as shown in FIG. 1. (Palumbo, S. L., Ebbinghaus, S. W. & Hurley, L. H. Formation of a unique end-to-end stacked pair of G-quadruplexes in the hTERT core promoter with implications for inhibition of telomerase by G-quadruplex-interactive ligands. *Journal of the American Chemical Society* 131, 10878-10891, doi:10.1021/ja902281d (2009)). That structure predicts a spectrum that would be a linear combination of the spectra of a parallel quadruplex, an antiparallel hybrid quadruplex and an 8 bp duplex hairpin. The predicted spectrum for that structure, shown in FIG. 2, differs significantly from the experimentally observed spectrum, especially in the amplitude at 260 nm. For comparison, the spectrum of a three-quartet parallel quadruplex formed by a sequence variant of the c-myc promoter sequence, 1XAV ENREF 15 (Ambrus A, Chen D, Dai J, Jones R A, Yang D (2005) Solution structure of the biologically relevant G-quadruplex element in the human c-MYC promoter. Implications for G-quadruplex stabilization. *Biochemistry* 44:2048-2058. doi: 10.1021/bi048242p), is shown. The shape of that spectrum is similar to the observed hTERT spectrum but the amplitude at 260 nm differs dramatically. The difference in amplitudes can be quantitatively explained if the hTERT structure contains 9 stacked quartets, a structure that might result from the presence of three contiguous parallel quadruplexes that stacked upon one another. Such a structure is a reasonable alternative to the one shown in FIG. 1.

c. Characterization of the hTERT Promoter by Sedimentation Velocity Ultracentrifugation FIG. 3 shows the results of characterization of the hTERT promoter by sedimentation velocity ultracentrifugation. The distribution (c(s)) of sedimentation coefficients is shown and reveals a major species along with a small amount of higher-order species. Analysis of these data using a model of discrete noninteracting species yielded an $S_{20,w}$ value of 4.05±0.04 for the major (77%) component. The frictional ratio of this hydrated structure is 1.2, indicative of a non-spherical, asymmetric object (Schuck, P. Size-distribution analysis of macromolecules by sedimentation velocity ultracentrifugation and lamm equation modeling. *Biophysical Journal* 78, 1606-1619, doi:10.1016/50006-3495(00) 76713-0 (2000)). The mass of this species corresponds to the molecular weight of a single strand of the sequence shown in FIG. 1, indicating a folded unimolecular structure. Steady-state fluorescence polarization experiments yielded a rotational relaxation time of 30.9±4.1 ns, compared to a predicted value of 14.6 ns for an equivalent sphere. The ratio of these two values, 2.1±0.3, again indicates that the folded unimolecular structure is asymmetric.

Minor amounts (14%) of faster sedimenting species (probably aggregates) are seen, along with minor amounts of slower sedimenting material (probably incompletely folded products). We previously determined that human telomere sequences can form structures with three contiguous quadruplexes with $S_{20,w}$ values of 3.49 and 3.87 for antiparallel and all-parallel conformations, respectively (Petraccone, L., Trent, J. O. & Chaires, J. B. The tail of the telomere. *Journal of the American Chemical Society* 130, 16530-16532, doi: 10.1021/ja8075567 (2008)). These values suggest that the hTERT sequence forms a three quadruplex structure of some form, consistent with the conclusion based on CD spectra. A three-dimensional molecular model of mixed quadruplex-duplex structure shown is FIG. 1, optimized with explicitly hydrated molecular dynamics, is predicted to have an $S_{20,w}$ value of 3.2, significantly lower than experimentally observed value, again suggesting that the model is inconsistent with the observed behavior. For mutated sequences, discrete sedimentation coefficients are reduced to 3.5-3.6±0.04 $S_{20,w}$ (FIG. 3). For the mutated sequences of the hTERT promoter in FIG. 3, I=hTERT-2M, II=hTERT+2E, and III=hTERT+1. The differences in $S_{20,w}$ between the wild-type and mutant sequences are significant (p<0.001) given the precision of sedimentation velocity measurements and as determined by a one-way analysis of variance of the experimental data. The reduced $S_{20,w}$ values indicate hydrodynamically expanded structures compared to the wild-type sequence. Mutations thus seem to unfavorably affect packing of the multiple quadruplex structures. In addition to the reduction in $S_{20,w}$ values, mutant sequences show a greater propensity to form aggregated structures, with a concomitant reduction (by 10-15%) in the amount of the major unimolecular species.

d. Molecular Modeling

Figure 4B:
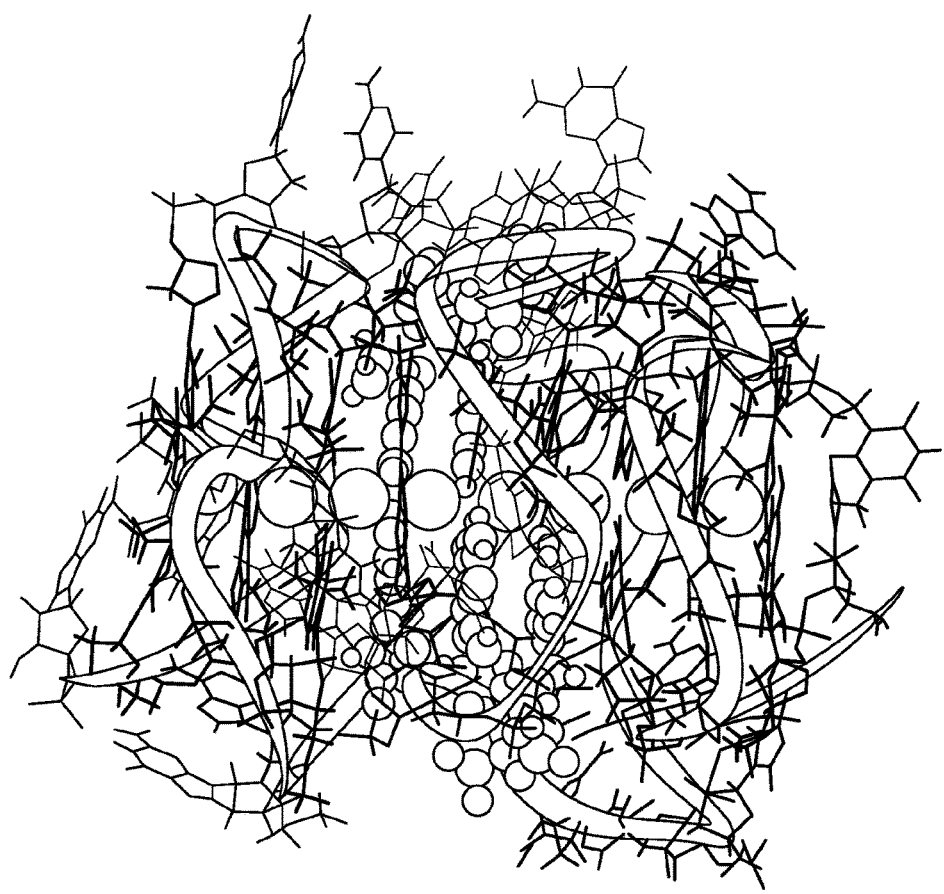
FIG. 4. Molecular model for the hTERT promoter structure featuring three stacked parallel quadruplexes (right). The model predicts $S_{20,w}$=4.00±0.1, in excellent agreement with the observed value of the wild-type sequence. A schematic of the structure is shown on the left side, with the sites of mutations marked with arrows.
Figure 4A:
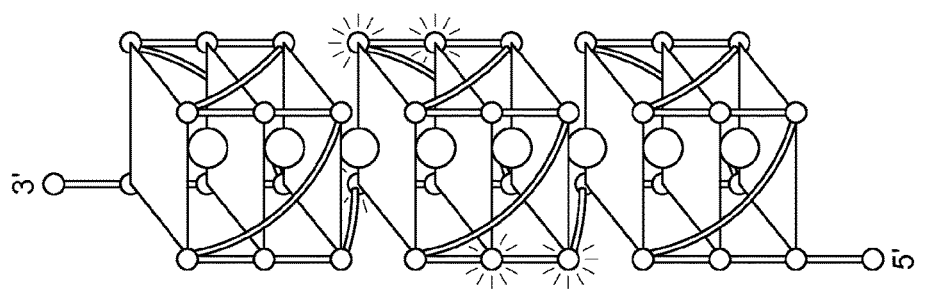

Molecular modeling simulations were used to construct a more realistic detailed model of the structure formed by the hTERT core promoter that is consistent with the biophysical data using computational protocols (Le, H. T., Buscaglia, R., Dean, W. L., Chaires, J. B. & Trent, J. O. Calculation of hydrodynamic properties for G-quadruplex nucleic acid structures from in silico bead models. *Topics in current chemistry* 330, 179-210, doi:10.1007/128_2012_351 (2013)). The three-stacked parallel quadruplex model (FIG. 4) was built using known structures with adjustment of the loop regions to be consistent with Micheli et al (Micheli, E., Martufi, M., Cacchione, S., De Santis, P. & Savino, M. Self-organization of G-quadruplex structures in the hTERT core promoter stabilized by polyaminic side chain perylene derivatives. *Biophysical chemistry* 153, 43-53, doi:10.1016/j.bpc.2010.10.003 (2010)). The 5'-region is the same as the reported NMR structure for a portion of the hTERT promoter sequence (Lim, K. W. et al. Coexistence of two distinct G-quadruplex conformations in the hTERT promoter. *Journal of the American Chemical Society* 132, 12331-12342, doi:10.1021/ja101252n (2010). It is possible to construct a model that has all of the major mutations in the central quadruplex G-quartets. The model was fully stable while running a fully solvated 20 ns molecular dynamics trajectory with no disruption to quadruplex or inter-quadruplex stacking. This was followed by 10 ns of accelerated molecular dynamics to sample more conformational space of the loop regions. Hydropro calculations, using our quadruplex optimized calibration protocol, on 5,000 snapshots from the accelerate molecular dynamics trajectory revealed a range of $S_{20,w}$ values of 3.95-4.03, in excellent agreement with what was experimentally observed. The resulting structures are (and have to be) extremely compact to maintain these sedimentation values. This structure is predicted to have a rotation relaxation time of 34.4 ns, in excellent agreement with the experimentally measured value. Several alternate models were explored, but none of these predicted hydrodynamic values that agreed with the experimentally measured values. For example, one alternate model was created that maintained the same three quadruplexes but did not have any inter-quadruplex stacking. The calculated $S_{20,w}$ was 3.1 for this "beads-on-a-string" parallel structure, far from the experimental value and indicating that noninteracting quadruplex formation alone cannot account for the biophysical data. Similarly, a three-quadruplex structure with antiparallel quadruplex units could not account for the observed biophysical data.

Sedimentation and circular dichroism data are thus entirely consistent with a compact structure in which three parallel quadruplexes are tightly stacked on one another. The complex quadruplex-duplex structure (Xing, M. et al. BRAF V600E and TERT Promoter Mutations Cooperatively Identify the Most Aggressive Papillary Thyroid Cancer With Highest Recurrence. *Journal of clinical oncology: official journal of the American Society of Clinical Oncology* 32, 2718-2726, doi:10.1200/JCO.2014.55.5094 (2014)) and the multiple "beads-on-a-string" quadruplex structure (Nygren, J., Svanvik, N. & Kubista, M. The interactions between the fluorescent dye thiazole orange and DNA. *Biopolymers* 46, 39-51, doi:10.1002/(SICI)1097-0282(199807)46:1<39:: AID-BIP4>3.0.CO;2-Z (1998)) are inconsistent with our biophysical data.

Figure 5B:
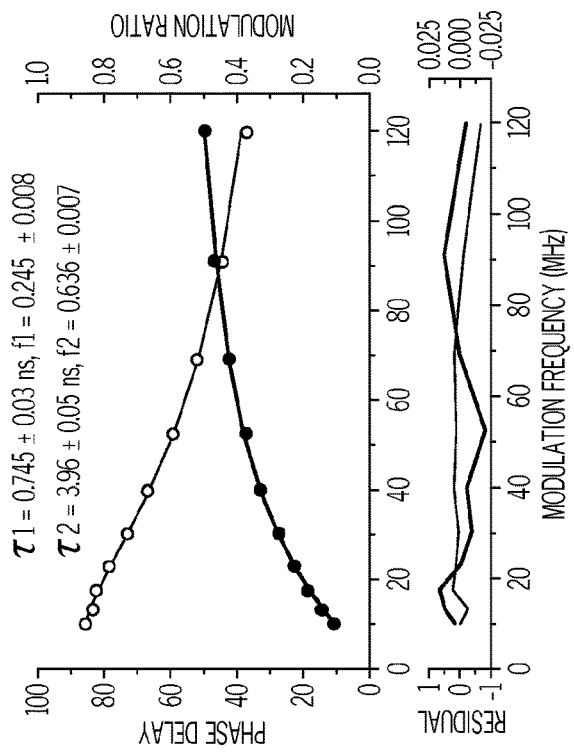
FIG. 5. Representative response curves for phase delay and modulation ratio for determination of fluorescence lifetimes of thiazole orange bound to oligonucleotide 1XAV.
(FIG. 5A) and hTERT (FIG. 5B). The points represent the experimental data and the lines represent the best fit of the data points using the lifetimes and fractional contributions of each to a two-lifetime model. The lower panels show the residuals for each fit. The data were analyzed using the program Vinci Beta 1.7. Experimental conditions: 0.9 μM 1XAV, 0.3 μM thiazole orange; 1.4 μM hTERT, 0.4 μM thiazole orange. Determinations were made at room temperature (~21° C.). Both samples were in tBAP folding buffer, 200 mM KCl, 20% sucrose, pH 7.0. Lifetimes and fractions determined by non-linear least squares analysis are shown in the figures.
Figure 5A:
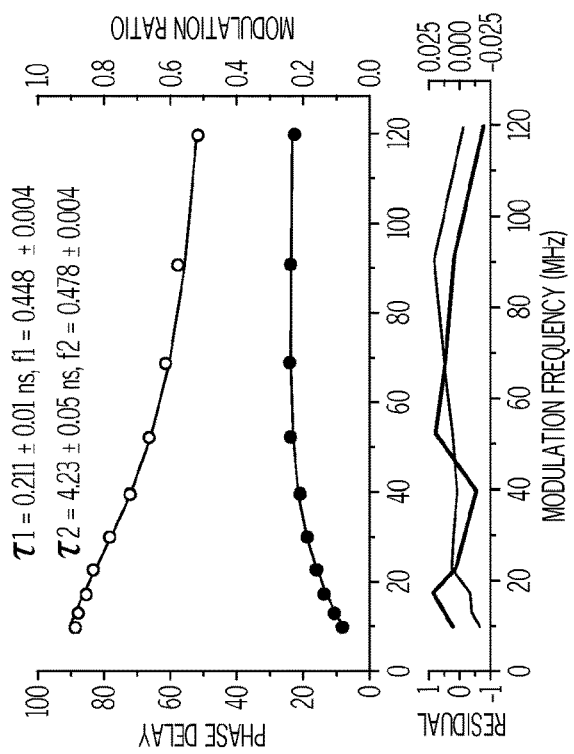

Surprisingly, the mutations shown in FIG. 1 have little effect on the thermal stability of the hTERT structure (FIG. 5A). Under the ionic conditions used, thermal denaturation is incomplete at 95° C. and the melting temperature at the transition midpoint is greater than 90° C. However if the sequence 5'-GGGGCTGGGCCGGGGACCCGGG is used to form a monomeric quadruplex mutations dramatically decrease the thermal stability (FIG. 5B). That sequence would encompass the central quadruplex-forming sequence in the hTERT promoter and readily forms a single parallel quadruplex structure. In the full length hTERT structure, allosteric interactions between contiguous quadruplexes apparently mask the destabilizing effects of the mutations. Additionally, we have shown that low-resolution techniques, such as melting, mask the complexity of quadruplex ensemble components (Dailey, M. M., Miller, M. C., Bates, P. J., Lane, A. N. & Trent, J. O. Resolution and characterization of the structural polymorphism of a single quadruplex-forming sequence. *Nucleic acids research* 38, 4877-4888, doi:10.1093/nar/gkq166 (2010)).

While the mutations can be accommodated by alternate G-quadruplex formation in the longer sequences (which could account for the similar thermal stability), this would require a reduction to a two-tetrad stacked central quadruplex or by mixed guanine-adenine stacking. However, this would require changes in the connecting and internal loop structures of the central quadruplex, thus lowering the $S_{20,w}$ value due to longer loops and decreased compactness, as is in fact observed in FIG. 3. Such alterations would affect recognition elements, protein binding and/or stability Detailed structural studies on quadruplex forming sequences in promoter regions have been limited to single quadruplex structures and often these shorter sequences are highly manipulated to reduce polymorphism. This study indicates that the longer promoter region quadruplex-forming sequences may be much more complicated and more biologically contextual. This may well be a general phenomenon as these extended quadruplex-forming sequences are common in the promoters of proto oncogenes that have not been previously examined in this detail.

More than 90% of human tumors overexpress telomerase, as do rapidly dividing cells such as stem cells and germ cells (Shay, J. W. & Bacchetti, S. A survey of telomerase activity in human cancer. *Eur J Cancer* 33, 787-791, doi:10.1016/S0959-8049(97)00062-2 (1997) and Hiyama, E. & Hiyama, K. Telomere and telomerase in stem cells. *Br J Cancer* 96, 1020-1024, doi:10.1038/sj.bjc.6603671 (2007)). The mechanism by which hTERT expression is dysregulated has been largely unknown. The data presented here indicate that the common mutations in the hTERT promoter occur in a quadruplex structure in this region. It is possible, by altering recognition elements and stability of this region, that the "transcriptionally active" duplex DNA structure with the E-twenty six (ETS) binding site would be favored. Importantly, ETS binding likely helps stabilize the double stranded (transcriptionally active) structure. This loss of quadruplex stability could abrogate the gene silencing effects of quadruplex formation, allowing increased hTERT expression. Because of its ubiquitous overexpression and its critical role in almost all tumors, telomerase is an excellent therapeutic target. The concept of reversing promoter silencing via mutations that cause quadruplex destabilization is an exciting new paradigm and provides the first plausible rationalization of mutation mediated gene transcription by quadruplex control.

Example 2

Common hTERT Promoter Mutations Represent a Novel Therapeutic Target Materials and Methods Oligonucleotides The hTERT wild type and mutated oligonucleotides were purchased from Oligos etc. (Wilsonville, Oreg.). The lyophilized oligonucleotides were reconstituted in sterile nuclease free $H_2O$ (Millipore, MA) at 500 µM and storage at $-20°$ C.

Circular Dichroism (CD) Spectrometry:

The oligonucleotide samples were diluted at 5 µM in TM buffer (50 mM TRIS-HCl/2.5 mM $MgCl_2$, pH7.0), denatured and annealed overnight at room temperature (RT). The concentration was verified by measuring the OD at 260 nm in a Diode Spectrometer before the CD measurement on a Jasco J-710 spectropolarimeter in a 1 cm Quartz cuvette. The spectra were recorded from 220 nm to 340 nm at $20°$ C.; four spectra were averaged for each reading. The molar extinction coefficients were calculated using the IDT calculator (IDT.com, oligoAnalyser3.1). The CD data were normalized to strand concentration and are expressed in Molar ellipticity [θ] ($deg \times cm^2 \times decimole^{-1}$).

Oligonucleotide Structure

Oligonucleotides were 5' end labeled with $^{32}$P-ATP (3 µEu) using T4 PNK and 1x kinase buffer for 20 minutes at $37°$ C. Unincorporated nucleotides were removed using G-25 Sephadex columns. Samples (4,000 cpm) were then mixed with cold oligonucleotide, boiled for ten minutes and allowed to anneal overnight. An equal volume of 2x glycerol dye was added and run on a 15% native acrylamide gel at 250V for 3 h. The bands were visualized by exposing a Kodak phosphor-imager screen and scanned using a Molecular Imager (Pharos FX Plus, Bio-Rad) then to Kodak film for 12 h at $-80°$ C.

Electrophoretic Mobility Shift Assay (EMSA)

The PCR product of a 134 bp hTERT promoter sequence was incubated with 100000 cpm of 5'-end $^{32}$P-labeled hTERT wild type or mutated oligonucleotide in 20 mM HEPES (pH 7.9), 25 mM KCL, 2 mM $MgCl_2$, 0.1 mM EDTA, 0.2 mM DTT, 2 mM spermidine and 10% glycerol for 15 min at $37°$ C. For the competition assay, increasing concentrations of "cold" hTERT oligonucleotide (1 nM to 1 µM) were added to each labeled oligonucleotide and incubated for an additional 15 min. After incubation, an equal volume of 2x glycerol dye was added. Complexes (50000 cpm) were resolved by electrophoresis on a 5% non-denaturing polyacrylamide gel, and visualized as described above.

Cell Culture

Four leukemia cell lines were investigated: U937 (Histiocytic Lymphoma, HL), Molt-4 (acute-T-lymphoblastic leukemia, ALL), HL-60 (Acute Promyelocytic leukemia, APL) and Raji (Burkitt's lymphoma, BL), all obtained from American Type Culture Collection (ATCC, Manassas, Va.). The cell lines were maintained in culture in RPMI-1640/10% FBS/penicillin-streptomycin (all from HyClone, Utah) at $37°$ C./5% $CO_2$ in humid atmosphere and were evaluated at exponential growth.

MTT Assay

Cells were seeded at $5 \times 10^3$ cells/well in 96-well flat bottom plates in the presence of different concentrations of oligonucleotides for 24 h up to 5 days as specified in the text. Untreated cells were used as control, and media for blank. Cell proliferation was evaluated by using MTT [3-(4,5-Dimethylthiazol-2-yl) 2,5-diphenyltetrazolium Bromide) Sigma-Aldrich, St Louis, Mo.], as known in the art. Data are shown as percent of the untreated control for an average of at least 3 experiments+/−Standard deviation.

Western Blot

U937 were cultured at $1 \times 10^5$ cells/ml in the presence of Pu27, Pu5− or Pu9− (10 µM) compared to untreated for 3 days. Total protein lysates was prepared using M-Per lysis buffer (Pierce) containing protease inhibitors (Roche) according to manufacturer instruction and quantified using Coomassie Protein reagent (Thermo). Equal amounts of protein were run in 4-15% gradient gel (Bio-Rad) for 1 h at 70 V, then transferred to PVDF membrane using an iblot (Invitrogen™). The membrane was blocked with 5% non-fat dry milk, washed in PBST (PBS/0.05% Tween), hybridized for 1 h at RT with anti-c-MYC antibody (Santa Cruz), followed by washes in PBST, then incubated 1 h at RT with goat anti-mouse antibody. The protein was visualized using femto chemiluminescence reagent (Pierce).

Statistical Analysis

Except for the gene array analysis, all data are expressed as mean+/−standard deviation (SD) comparison between untreated and treated was assessed using unpaired two-tailed Student T-test and were considered significant at p-value <0.05.

Figure 6A:
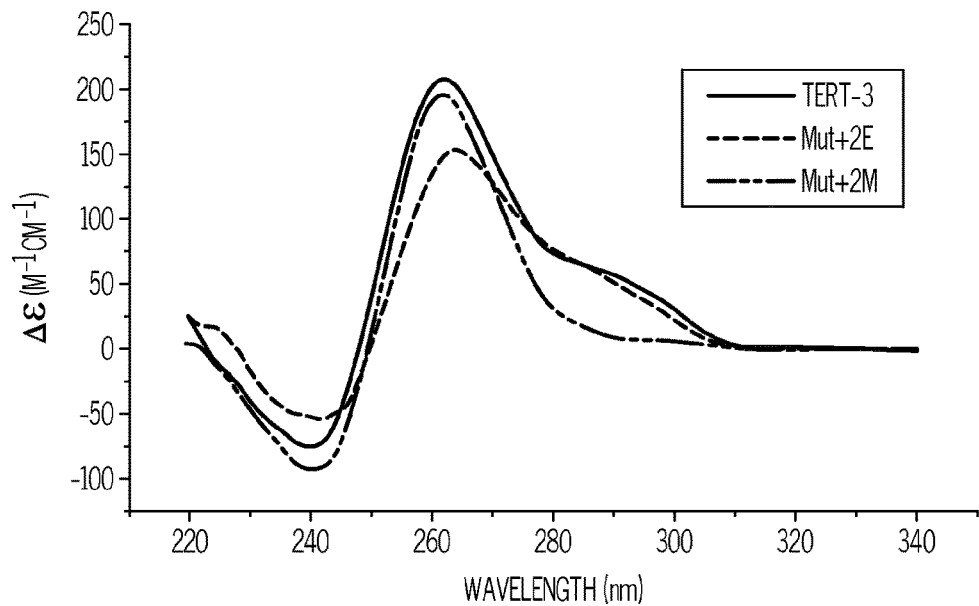
FIG. 6A depicts the sedimentation equilibrium analysis of the WT and mutant hTERT structures.
Figure 6B:
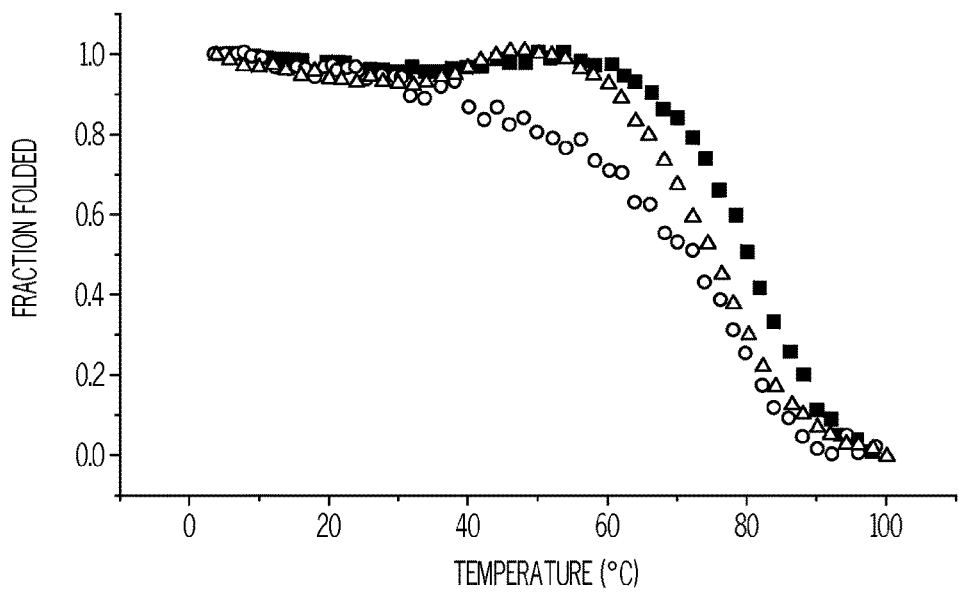
FIG. 6B shows the thermal denaturation characteristics of the wild-type (WT) hTERT sequence (squares) and two mutation containing oligonucleotides, hTERT-2M (triangles) hTERT+2E (circles).
Figure 7:
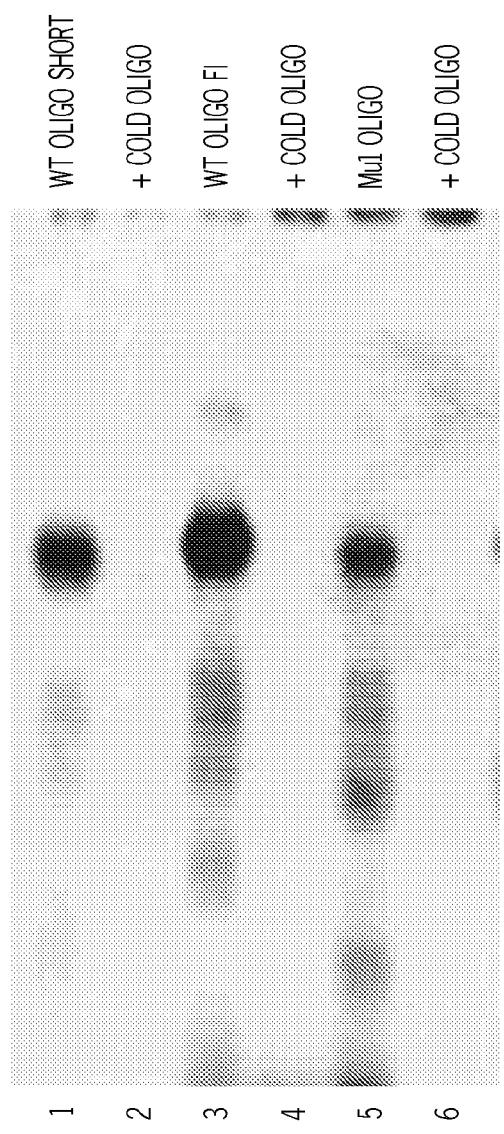
FIG. 7. hTERT Oligos Bind Specifically to Their DS Parent Sequence.
Figure 8:
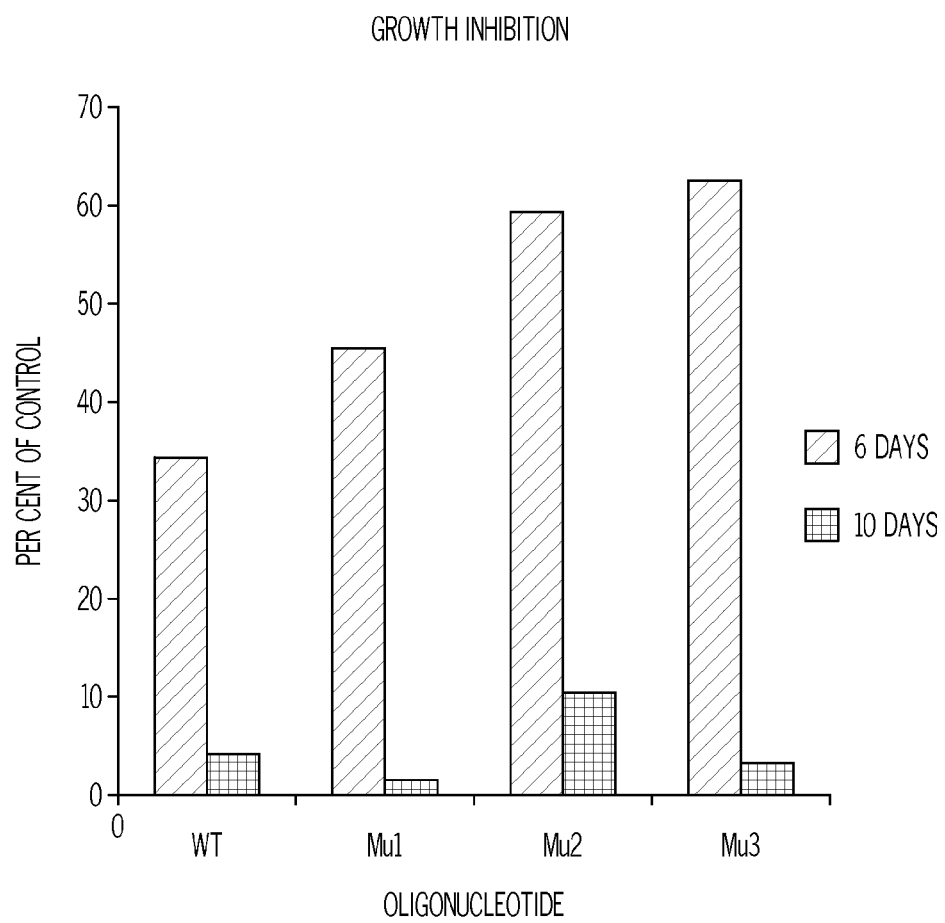
FIG. 8. Oligonucleotides encoding the hTERT promoter quadruplex-forming sequence selectively inhibit growth of cells with hTERT promoter mutations.
Figure 9:
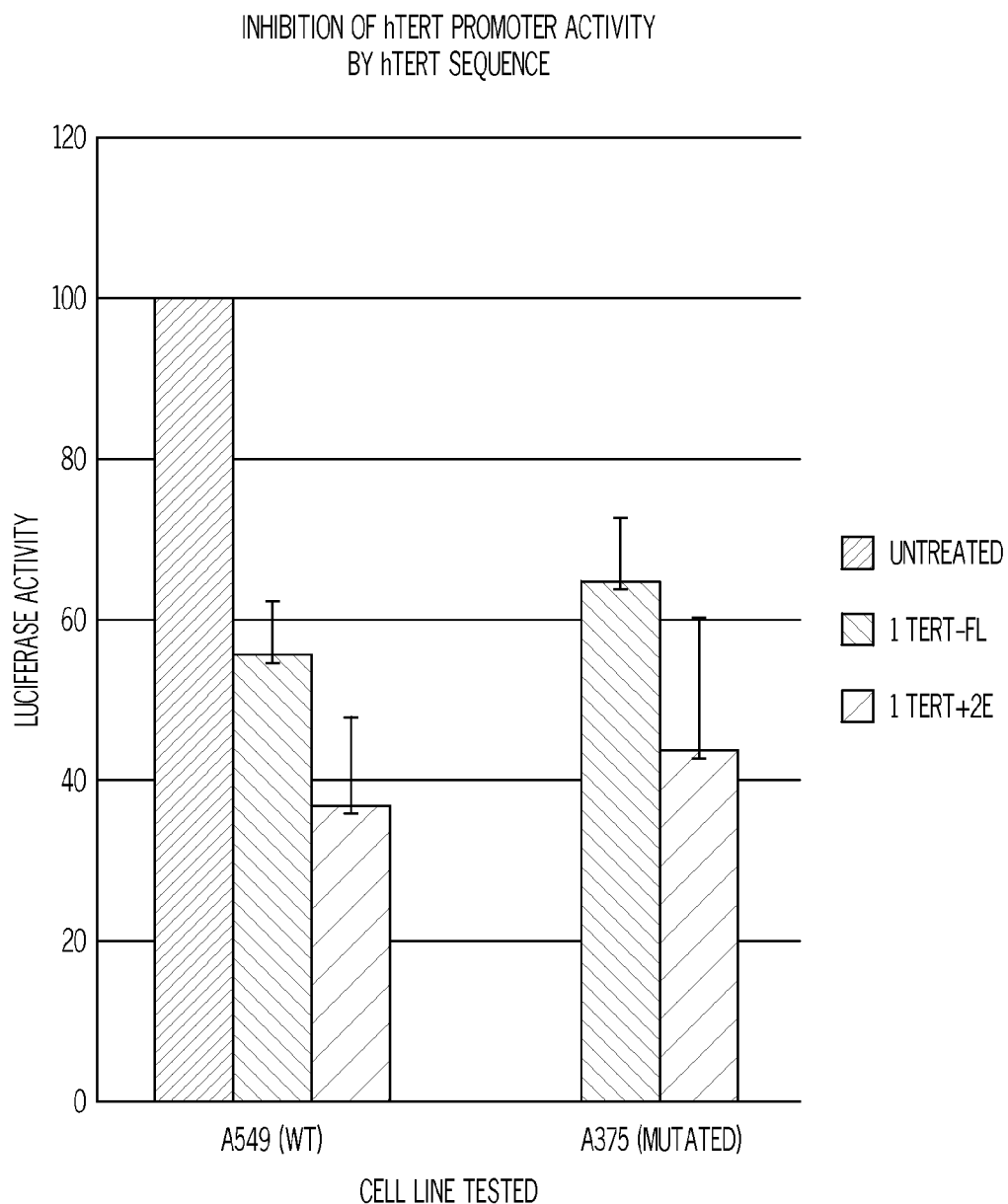
FIG. 9. Inhibition of hTERT promoter activity by hTERT quadruplex-forming oligonucleotides. Luciferase expression vector had normal hTERT promoter sequence.

Results and Discussion a. hTERT Mutations Destablize Quadruplex and Increase Promoter Activity The hTERT promoter mutations occur in a 67 bp sequence of the hTERT promoter that has previously been shown to form quadruplex DNA. FIG. 6 shows the results of our study of the structure and stability of hTERT and mutant sequences. FIG. 6A shows the sedimentation equilibrium analysis of the WT and mutant hTERT structures. The data clearly show that the mutation of the wild-type TERT sequence significantly destabilizes the quadruplex structure. $S_{20,w}$ values for folded mutant sequences are significantly reduced from 4.05±0.04 to 3.3-3.4±0.04. FIG. 6B shows the thermal denaturation characteristics of the wild-type (WT) hTERT sequence (squares) and two mutation containing oligonucleotides, hTERT-2M (triangles) and hTERT+2E (circles). There is a marked decrease in the stability of the mutated oligonucleotides. All of the biophysical changes were reversed in the presence of TMPyP4, a quadruplex stabilizing compound. These results indicate that, although the mutated sequences do form quadruplex structures, they are significantly less stable than the wild type sequence. This instability likely drives the equilibrium from quadruplex towards the transcriptionally active duplex structure.

b. The WT hTERT Promoter Quadruplex-Forming Oligonucleotide Binds Specifically to its Double Stranded "Parent" Sequence We used gel shift analysis to demonstrate the specificity of the interaction between the hTERT promoter sequence and its double stranded "target" sequence. As shown in FIG. 7, oligonucleotides encoding the entire WT quadruplex forming sequence (67 bp in length) and a shorter WT oligonucleotide (21 bp) bind to the parent sequence (lanes 1 and 3). This binding can be competed by cold oligonucleotide (lane 2 and 4) indicating that the binding is sequence specific. In lanes 5 and 6, a similar experiment is performed with an oligonucleotide containing one of the melanoma mutations binding to a mutated parent sequence. The resulting binding appears to be equally specific as that observed for the WT sequences. In order to determine whether this interaction occurred by intramolecular quadruplex formation or by strand invasion we performed binding experiments using hTERT oligonucleotides labelled with the DNA crosslinker, 3-cyanovinyl-carbazole (Vieregg J R, Nelson H M, Stoltz B M, Pierce N A. Selective nucleic acid capture with shielded covalent probes. Journal of the American Chemical Society 2013; 135:9691-9). When crosslinking was activated by UV exposure, the G-rich oligonucleotide bound only to the C-rich strand, but not to the G-rich strand. This experiment clearly demonstrates that the hTERT oligonucleotide is binding to the complementary C-rich strand by strand invasion. This result has very important therapeutic implications because the DNA-DNA interaction of strand invasion is via Watson Crick binding and is absolutely sequence specific. This interaction of the hTERT oligonucleotide with its "parent" sequence would be expected to stabilize the quadruplex structure in the "off" position. In this setting, the specific stabilization of the endogenous quadruplex structure by the exogenous oligonucleotide, provides the opportunity to inhibit hTERT transcription in a "gene-specific" manner.

c. Stabilization of the hTERT Quadruplex-Forming Sequence with Sequence-Specific Oligonucleotides Inhibits the Growth of Cells with hTERT Promoter Mutations Because of our previous experience with the growth inhibition by quadruplex-forming oligonucleotides, we were interested in characterizing the effect of hTERT oligonucleotides on the growth of cells with wild type and mutated hTERT promoter sequences. We reasoned that cells with the mutated promoter sequence might be more sensitive to stabilization of the quadruplex forming sequence since they would be overexpressing telomerase which would provide stimulus for telomere lengthening and nontelomeric telomerase effects. Indeed, this was the case. As shown in FIG. 8, the telomere promoter quadruplex-forming oligonucleotides (WT and three mutant sequences) inhibited the proliferation of cell lines with mutated promoter sequences to a greater extent than those with a wild type hTERT promoter, suggesting that stabilization of the quadruplex structure in the hTERT promoter results in decreased expression and telomerase activity. For the mutated sequences of the hTERT promoter, Mu1=hTERT-2M, Mu2=hTERT+2E, and Mu3=shTERT+1. The IC50 of cells with mutated promoter was in the 1-2 mM range. This dramatic difference indicates that these oligonucleotides may represent novel growth inhibitory molecules.

d. hTERT Promoter Quadruplex-Forming Oligonucleotides Inhibit hTERT Promoter Activity In order to characterize the effect of the hTERT quadruplex-forming oligonucleotides, we tested their effect on hTERT promoter/luciferase expression vectors. As noted above, this approach has been used to document induced overexpression of the luciferase promoter by the mutated sequences. Using reporter vectors in which luciferase is expressed under the control of the wild type hTERT promoter sequence (Veldman T, Horikawa I, Barrett J C, Schlegel R. Transcriptional activation of the telomerase hTERT gene by human papillomavirus type 16 E6 oncoprotein. J Virol 2001; 75:4467-72), we have shown (FIG. 9) that oligonucleotides comprised of the wild type hTERT quadruplex-forming sequence can inhibit promoter activity.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A composition comprising: (i) at least two different isolated oligonucleotides and each oligonucleotide has at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12, (ii) a carrier, and (iii) a growth inhibiting agent.

2. The composition of claim 1, wherein the composition comprises at least three different isolated oligonucleotides and each oligonucleotide has at least 80% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

3. The composition of claim 1, wherein at least one isolated oligonucleotide has at least 90% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

4. The composition of claim 1, wherein at least one isolated oligonucleotide has at least 95% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

5. The composition of claim 1, wherein at least one isolated oligonucleotide has at least 98% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

6. The composition of claim 1, wherein at least one isolated oligonucleotide has at least 99% nucleic acid sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

7. The composition of claim 1, wherein at least one isolated oligonucleotide has a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

8. The composition of claim 1, wherein at least one isolated oligonucleotide has at least 80% nucleic acid sequence identity with a sequence selected from the group consisting of SEQ ID NO: 1, SEQ ID NO: 2, SEQ ID NO: 3, SEQ ID NO: 7, and SEQ ID NO: 8.

9. The composition of claim 1, wherein the growth inhibiting agent is a chemotherapeutic agent.

10. A method of inhibiting cell growth, comprising contacting a cell with the composition of claim 1.

11. A method of inhibiting telomerase activity of a cell, comprising contacting the cell with the composition of claim 1.

12. The method of claim 10, wherein the composition comprises an isolated oligonucleotide with a sequence selected from the group consisting of SEQ ID NO: 1, SEQ ID NO: 2, SEQ ID NO: 3, and SEQ ID NO: 8.

13. The method of claim 11, wherein the composition comprises an isolated oligonucleotide with a sequence selected from the group consisting of SEQ ID NO: 1, SEQ ID NO: 2, SEQ ID NO: 3, and SEQ ID NO: 8.

14. The method of claim 10, wherein the composition comprises an isolated oligonucleotide with a sequence selected from the group consisting of SEQ ID NO: 1, SEQ ID NO: 2, SEQ ID NO: 3, SEQ ID NO: 7, and SEQ ID NO: 8.

15. The method of claim 10, wherein the composition comprises an isolated oligonucleotide with a sequence selected from the group consisting of SEQ ID NO: 1, SEQ ID NO: 2, SEQ ID NO: 3, SEQ ID NO: 7, and SEQ ID NO: 8.

16. The composition of claim 1, wherein the composition comprises an isolated oligonucleotide with a sequence selected from the group consisting of SEQ ID NO: 1, SEQ ID NO: 2, SEQ ID NO: 3, SEQ ID NO: 7, and SEQ ID NO: 8.

17. The composition of claim 1, wherein the composition comprises (a) two or more isolated oligonucleotides selected from the group consisting of SEQ ID NO: 1, SEQ ID NO: 2, SEQ ID NO: 3, SEQ ID NO: 7, and SEQ ID NO: 8 and (b) a chemotherapeutic agent.

18. The composition of claim 1, wherein the composition comprises an isolated oligonucleotide with a sequence selected from the group consisting of SEQ ID NO: 1, SEQ ID NO: 2, SEQ ID NO: 3, and SEQ ID NO: 8.

19. The composition of claim 1, wherein the composition comprises (a) two or more isolated oligonucleotides selected from the group consisting of SEQ ID NO: 1, SEQ ID NO: 2, SEQ ID NO: 3, and SEQ ID NO: 8 and (b) a chemotherapeutic agent.

20. The composition of claim 2, wherein the composition comprises (a) two or more isolated oligonucleotides selected from the group consisting of SEQ ID NO: 1, SEQ ID NO: 2, SEQ ID NO: 3, and SEQ ID NO: 8 and (b) a chemotherapeutic agent.

21. The composition of claim 1, wherein at least one oligonucleotide is no more than 68 nucleotides long.

* * * * *